US009352756B2

(12) United States Patent
Grant

(10) Patent No.: US 9,352,756 B2
(45) Date of Patent: May 31, 2016

(54) PASSENGER OCCUPANCY IDENTIFICATION SYSTEM

(71) Applicant: TrainFX Ltd., Derby, Derbyshire (GB)

(72) Inventor: Zeph Grant, Leicestershire (GB)

(73) Assignee: TrainFX Ltd., Derby, Derbyshire (GB)

( * ) Notice: Subject to any disclaimer, the term of this patent is extended or adjusted under 35 U.S.C. 154(b) by 0 days.

(21) Appl. No.: 14/072,984

(22) Filed: Nov. 6, 2013

(65) Prior Publication Data

US 2014/0125355 A1    May 8, 2014

(30) Foreign Application Priority Data

Nov. 7, 2012    (GB) .................................... 1220047.3

(51) Int. Cl.
| G01R 27/26 | (2006.01) |
| B61D 33/00 | (2006.01) |
| B60R 21/015 | (2006.01) |
| G01N 27/22 | (2006.01) |
| B60N 2/00 | (2006.01) |
| B64D 11/00 | (2006.01) |
| B64D 11/06 | (2006.01) |
| B61D 41/02 | (2006.01) |
| B60N 2/24 | (2006.01) |
| H04W 4/00 | (2009.01) |
| B64D 45/00 | (2006.01) |

(52) U.S. Cl.
CPC ............ *B61D 33/0057* (2013.01); *B60N 2/002* (2013.01); *B60N 2/242* (2013.01); *B60R 21/01532* (2014.10); *B61D 41/02* (2013.01); *B64D 11/0015* (2013.01); *B64D 11/06* (2013.01); *G01N 27/22* (2013.01); *G01R 27/2605* (2013.01); *B64D 2045/007* (2013.01); *H04W 4/008* (2013.01)

(58) Field of Classification Search
CPC .......... B60N 2/002; B60N 2002/0272; B60R 21/0132; B60R 21/01516; B60R 21/01532; G01R 27/2605; G01N 27/22; B61D 33/0057
USPC ................. 340/667; 297/411.1, 445.1, 452.1; 324/661, 658, 665, 629, 679, 663, 686
See application file for complete search history.

(56) References Cited

U.S. PATENT DOCUMENTS

| 5,971,432 A * | 10/1999 | Gagnon et al. ................ 280/735 |
| 6,658,572 B1 | 12/2003 | Craig |
| 7,319,854 B2 * | 1/2008 | vonDoenhoff et al. ....... 455/345 |
| 8,170,745 B1 * | 5/2012 | Lors ............................... 701/36 |

(Continued)

FOREIGN PATENT DOCUMENTS

| EP | 1236609 A1 | 9/2002 |
| EP | 1301800 | 4/2003 |

(Continued)

*Primary Examiner* — Amy He
(74) *Attorney, Agent, or Firm* — Young Basile Hanlon & MacFarlane P.C.

(57) ABSTRACT

A seat for a passenger vehicle is provided that comprises a first sensor for detecting the presence or absence of an occupant in the seat and a second sensor for validating the seat occupancy. The seat further comprises a transmitter for transmitting a signal indicative of valid occupancy of the seat. The first sensor may be a non-contact, capacitive sensor and the second sensor may comprise a near-field communication device for receiving a seat validation code. A seat validation system may be established on a passenger vehicle such as a train, wherein a central controller may report on seat occupancy status for the vehicle.

20 Claims, 3 Drawing Sheets

(56) References Cited

U.S. PATENT DOCUMENTS

| | | | |
|---|---|---|---|
| 2004/0113634 A1* | 6/2004 | Stanley et al. | 324/661 |
| 2007/0241545 A1* | 10/2007 | Federspiel | 280/735 |
| 2007/0299586 A1* | 12/2007 | Griffin | 701/45 |
| 2008/0100425 A1* | 5/2008 | Kiribayashi | 340/425.5 |
| 2009/0088929 A1* | 4/2009 | Launay et al. | 701/49 |
| 2009/0132128 A1* | 5/2009 | Marriott et al. | 701/45 |
| 2011/0186374 A1* | 8/2011 | McCoy | 180/268 |
| 2011/0278884 A1* | 11/2011 | Marchesi | 297/135 |
| 2012/0242492 A1* | 9/2012 | Grunfeld | 340/667 |

FOREIGN PATENT DOCUMENTS

| | | |
|---|---|---|
| EP | 2090460 A1 | 8/2009 |
| EP | 2213503 A1 | 8/2010 |
| EP | 2351662 A1 | 8/2011 |
| JP | 5039033 A | 2/1993 |
| JP | 5073571 A | 3/1993 |
| WO | 0192900 A1 | 12/2001 |

* cited by examiner

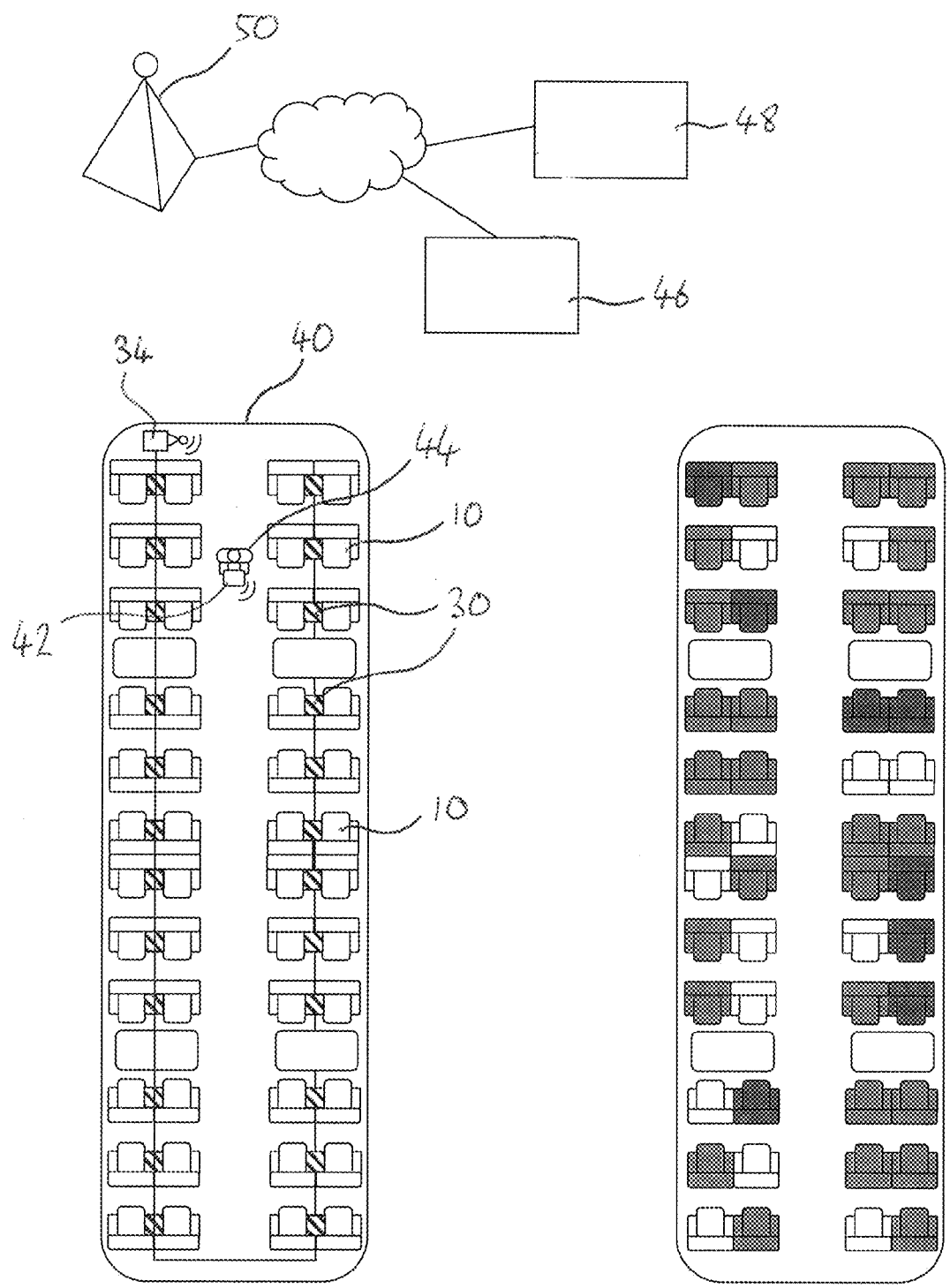
Figure 4a                    Figure 4b

PASSENGER OCCUPANCY IDENTIFICATION SYSTEM

TECHNICAL FIELD

The present invention relates to passenger occupancy identification systems and more particularly to seat occupancy systems suitable for use in passenger vehicles, vessels or aircraft.

BACKGROUND

Within the context of, for example, public transport, there exists a need to identify the number of passengers on board a vehicle. Within a number of train stations, attempts are made to monitor and identify the individuals boarding trains by controlling access to train platforms. Barriers and the like are used to allow passengers access to station platforms upon presenting a valid ticket.

However barriers only provide an indication of the number of passengers accessing platforms and do not provide an accurate indication of the actual number of people boarding a particular train. That is to say, having passed through a barrier, a passenger is usually presented with a number of platform options and timings of trains, all of which could be accessed despite only having a valid ticket for one specific journey.

Furthermore barriers could potentially be evaded, thereby casting doubt as to the true number of passengers on any particular route or train.

For the above reasons, at least in part, it remains normal practice to ensure that, as far as possible, each passenger's ticket is validated once on board a train by a conductor. However the manual checking of tickets is labor intensive and cannot provide a completely accurate picture of passengers embarking and disembarking since the manual checking of tickets incurs a significant time delay. Furthermore it is difficult to positively ascertain whether or not a particular passenger has disembarked at the correct station after his/her ticket has been initially checked.

The above problems result in a reduction in revenue for public transport operators, thereby reducing the available funds for maintaining and upgrading passenger vehicles and lines. Furthermore the uncertainty over occupancy of any particular vehicle represents a potential safety risk in the event of an emergency.

Whilst the above problems are described in relation to rail transport services, they are also applicable to passenger vehicles including buses, coaches, ferries and other vessels, as well as aircraft. It is acknowledged that some of the above problems are reduced by increasing security measures at airports, seaports, etc. in order to more tightly control access to such modes of transport. However such measures are typically labor intensive and reliant on manual checks.

BRIEF SUMMARY

It is an aim of the invention to provide for a positive determination of passenger occupancy for public transport service providers. It may be considered an additional or alternative aim of the invention to provide an automated on-board ticket validation system.

According to a first aspect of the invention there is provided a seat for a passenger vehicle, the seat comprising a first sensor for detecting the presence or absence of an occupant in the seat and a second sensor for validating or confirming the seat occupancy, wherein the seat further comprises a transmitter for transmitting a signal indicative of occupancy of the seat and/or validity of seat occupancy.

The first sensor may be a proximity sensor, such as a non-contact sensor. The first sensor may be a capacitive proximity sensor. The sensor may be calibrated over a range of between 5 and 50 cm. The sensor may be calibrated to determine a difference between different material properties in the sensed range. A predetermined threshold may be applied to discriminate between seat occupancy by a person and an inanimate object, such as a bag or the like.

The seat may comprise a rigid support and a resiliently deformable seating material thereon. The first sensor may be mounted on the rigid support.

The seat may comprise a base and a generally upright seat back. The first sensor may be provided in or under the base, for example on an underside thereof.

The second sensor may comprise a wireless communication device, e.g. a radio transmitter/receiver circuit. The second sensor may be arranged to receive or process a wireless signal from a portable validation device carried by the seat occupant. The portable validation device may comprise a ticket, card, tag or a portable data communication device having stored thereon a validation code. The second sensor may receive the validation code, for example automatically when the portable validation device is within range of, or proximate to, the second sensor.

The portable validation device may comprise an RFID chip. The second sensor may comprise a RFID interrogation device.

The second sensor may comprise a wireless communication device, such as, for example, a near-field sensor/communication device. The second sensor may have a range of 5 meters or less and typically 1 m or less, such as, for example, less than 50 or 20 cm. A short range device is beneficial in ensuring that adjacent seats are not accidentally validated by a single occupant. The second sensor may comprise a radio frequency antenna.

The second sensor may be provided in an arm rest portion of the seat. The second sensor may be embedded or encapsulated within the material of the arm rest or other seat portion.

The seat may comprise one or more further sensors, such as, for example a seat belt sensor, which may for example be provided with a seatbelt buckle or connector housing. In one embodiment, the further sensor may perform the function of the first sensor, either alone or in combination with another first sensor.

The seat may comprise a controller. The controller may be arranged to receive the signals from the first and second sensors and may control output/transmission of the signal indicative of valid occupancy of the seat. The seat may comprise a local data store, such as a non-volatile memory, which may be accessed by the controller.

The controller may control transmission of one or more of a plurality of signals. The signal may indicate both the occupancy status of the seat and also an indication of the validity of occupancy. A first signal may indicate valid occupancy of the seat, for example upon receiving the first and second sensor readings for the seat. A second signal may indicate invalid or un-validated occupancy of the seat, for example upon receiving the first sensor reading but no second sensor reading.

The seat may comprise a plurality of seats, each of which may have said first and second sensors. The plurality of seats may be provided in a side-by-side arrangement. A single controller may be provided for said plurality of seats. A seat pair may be provided in this manner.

According to a second aspect of the invention, there is provided a passenger vehicle or a cabin of a passenger vehicle, comprising a plurality of seats according to the first aspect, or any embodiment thereof.

The cabin/vehicle may comprise a central controller. The cabin/vehicle may comprise a central or common data store, which may be accessible by a central controller.

The cabin/vehicle may comprise a network, in which the seat controllers are connected to the central controller and/or common data store. The individual seat controllers may be connected in series to the central controller.

The central controller may be arranged to receive the signals indicative of valid occupancy of the seats from the plurality of seats.

Any or any combination of the central controller, common data store, the seat data store and/or the individual seat controllers may have stored thereon predetermined seat/passenger validation information. The predetermined validation information may comprise a plurality of codes which are valid for use by passengers on the vehicle for one or more journeys. In one embodiment, individual codes may be assigned to individual seats, for example in the event that seats have been reserved by a specific passenger for a specific journey.

The individual or central controller may compare the received signal with the predetermined/prestored validation information in order to determine whether or not the seat is validly occupied. In the event of a match with the prestored validation information, or an entry therein, a signal indicative of valid seat occupation may be output. In the event of no match, a signal indicative of invalid seat occupancy may be output. In the event that the received signal matches an entry of the prestored validation information, but not for the seat currently occupied, an alternative signal may be output accordingly.

The central controller may control output of a vehicle plan comprising the locations and occupancy status of the seats in the cabin/vehicle.

The central controller may comprise a transmitter, typically for wireless communication with one or more further devices or systems either on board or outside/remote of the vehicle. The central controller may communicate with one or more remote serves via a wide area network. The central controller may communicate with a remote monitoring facility.

According to a further aspect of the invention there is provided a passenger occupancy identification system comprising a plurality of seats according to the first aspect or a vehicle/cabin according to the second aspect.

The system may comprise an on-board network of seats in communication with the central controller. The central controller may comprise a transmitter/receiver for communication with a passenger occupancy information device/system. The device may comprise a display connected to or arranged for communication with the central controller.

In one embodiment, the passenger occupancy information device may comprise a communications/display device on board the vehicle. The device may have a screen for display of passenger occupancy information and/or a plan of the seats on the vehicle. The plan may indicate the occupation status of each seat according to the signals received by the central controller. Individual seats in the plan may be color coded or otherwise visibly coded to indicate their occupation states. The device may comprise a portable device, for example which is suitable be carried by a conductor.

The central controller may receive information pertaining to an occupation status change for each seat substantially in real-time.

In one embodiment the central controller communicates with a passenger occupancy information system which is remotely located. For example a central monitoring system or network may monitor information received from a plurality of vehicles. Information may be sent from the central controller to such a monitoring system using conventional wider area communication techniques, such as via GSM, 3G, EDGE or other mobile telecommunication technology or data transmission standards. Thus transport operators or service providers can monitor passenger levels remotely, substantially in real time. In one embodiment, occupancy information can be sent from one or more individual vehicle to a station or location at which the vehicle is due to arrive. The received information can be displayed on a passenger information display at that location, for example to indicate a number of seats available for occupancy on the vehicle.

The occupancy information may be transmitted to/from the vehicle, e.g. for validation and/or to communicate with a remote service provider. In one embodiment the service provider may be a ticket provider or the like. Thus the occupancy information may be used for the real-time purchase and/or reservation of seats whilst a train is in transit, for example prior to the arrival of the vehicle at a station or location.

In one embodiment, predetermined validation information may be updated in real-time, using the occupancy information. The predetermined validation information may comprise a plurality of codes which are valid for use by passengers on the vehicle for one or more journeys. Individual codes may be assigned to individual seats, for example in the event that seats have been reserved by a specific passenger for a specific journey. In one embodiment, individual codes may be updated in real-time based on the occupancy information sent to a location or station at which the vehicle is due to arrive. Thus the availability status of a seat may be updated in real-time, during the transit of the vehicle, allowing reserved seats that have not been validated to be re-sold to potential customers.

In one example, seats may have any or any combination of an occupied status, a validated status and/or a reserved status. Each seat may have a positive or negative condition for each status. Thus a service provider may use the information provided by the system according to the invention to release reserved seats which have not been occupied by the intended passenger. Thus the invention may allow seats to be reallocated if not validly occupied, thereby allowing efficient use of all seats on a vehicle.

In any aspect of the invention, the seats on board the vehicle may comprise, or be accompanied by, a display screen. The display screen may indicate the current occupancy status of the seat according to the occupancy validation signal from the seat controller or central vehicle/cabin controller. The display may also provide instruction to a passenger for validation of a ticket or other identification means.

Any of the optional features described above in relation to any one aspect of the invention may be applied to any other aspect, wherever practicable. It will be appreciated by the skilled reader that there are a number of alternative solutions for providing control and/or monitoring functions at seat level, at cabin/carriage/vehicle level, or else at a wider system level involving a number of vehicles.

For conciseness, the term "vehicle" is used herein to refer to any of: road or rail vehicles, such as buses, coaches, trams or trains; vessels, such as passenger boats or ferries; or aircraft.

BRIEF DESCRIPTION OF THE DRAWINGS

The description herein makes reference to the accompanying drawings wherein like reference numerals refer to like parts throughout the several views, and wherein:

FIG. 4a shows a schematic arrangement of the wider system in which the invention may be employed; and FIG. 4b shows an occupancy display generated by a controller according to one example of the invention.

DETAILED DESCRIPTION

The invention derives from the general premise that passenger vehicle occupancy can be better determined at seat level, instead of, or in addition to, monitoring footfall at vehicle stations or the like. The present invention thus provides a robust and accurate way of determining valid seat occupancy and monitoring the same at a vehicle or wider-system level.

Figure 1:
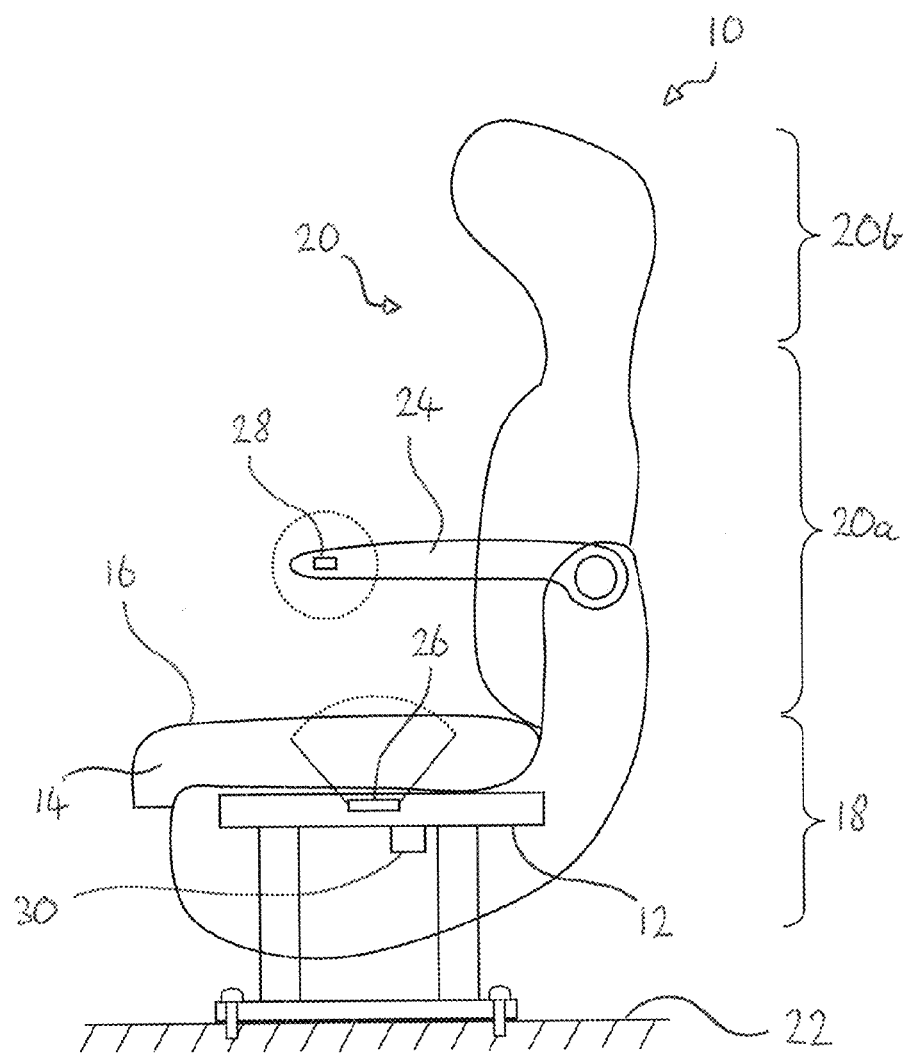
FIG. 1 shows a schematic side view of a seat according to one example of the invention.

Turning firstly to FIG. 1, there is provided a seat 10 according to one example of the present invention. The seat 10 comprises a rigid seat frame or support 12 and conventional upholstery 14, which may comprise padding, springs and/or webbing over the seat support/frame 12. A seat cover of leather or textile material is provided as an outer protective layer or cover 16 over the seat 10.

The seat 10 comprises a seat base 18 for supporting the majority of the weight of an occupant and a seat back 20. The seat base 18 is supported above a floor 22 or other support structure by one or more support members. The seat base 18 is generally horizontal or parallel with the floor or else tilted by a relatively small degree.

The seat back 20 is upstanding from the seat base 18 and may provide lumbar support/back support 20a and head rest 20b portions in a conventional manner.

An arm rest 24 is raised relative to the seat base 18 and projects forwardly of the seat back 20. The arm rest 24 may be attached, e.g. pivotably, to the seat back 20 as shown in FIG. 1 or else may be fixed to the seat base 18, to one side of the seat 10.

The seat support/frame 12 is typically rigidly affixed to the floor, for example by way of a plurality of bolts or other conventional fixings. The seat support/frame 12 may be released from the floor to allow removal, replacement/repositioning, refitting, repair or the like.

The seat 10 shown in FIG. 1 has a sensor, herein referred to as an occupancy detector, 26 mounted relative to the seat back 20 or seat base 18 so as to allow sensing of an occupied or unoccupied state of the seat. The occupancy detector 26 comprises a non-contact capacitive sensor. The sensor is mounted to a rigid portion of the seat support/frame 12. In the present embodiment the sensor is mounted to a cross bar within the seat base 18 but could equally be mounted in the seat back 20.

The occupancy detector 26 comprises an electrode/antenna to which a charged can be applied in the form of a proximity-type capacitive sensor. The capacitance of the antenna can thus be measured to determine the presence or absence of an occupant by the capacitive coupling between the occupant and the antenna. A single wire antenna may be used. The occupancy detector 26 may measure the capacitance to ground via the antenna and a threshold may be set which is indicative of the presence of an occupant in the seat. In one example, the antenna can be repeatedly charged and discharged such that the discharge current can be monitored and changes in the charge-discharge cycle (i.e. the charge-discharge waveform) can be assessed to determine whether any change exceeds a threshold indicative of the presence of an occupant within the seat.

By careful design of the antenna used on the proximity sensor it is possible to control the sensing range to be just greater than the seat cushion. In typical examples of the invention the sensing range can be set at a suitable range between 5 and 30 cm, and typically in the range 10-20 cm. However it will be appreciated that the precise range will be dependent on the construction of the seat itself and will vary between different implementations.

At such ranges the capacitive effect of the human body to ground is much higher than that of other objects, such as baggage, coats, etc. and so threshold values can be set to ensure that the sensor can discriminate between an occupant and other such objects.

Figure 2:
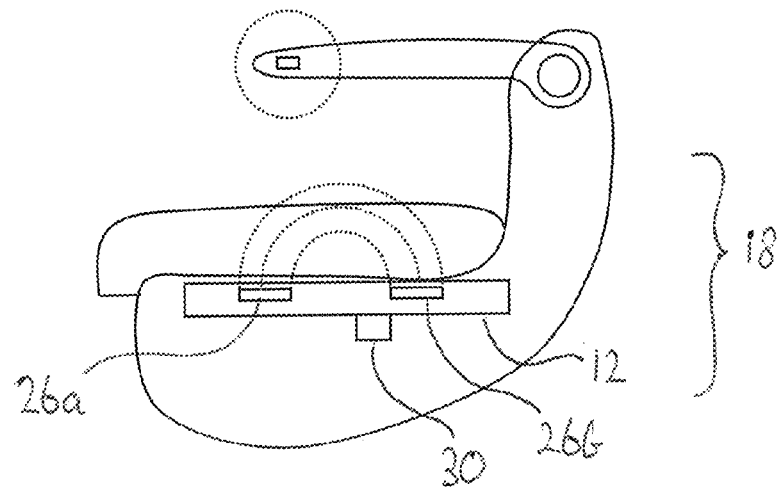
FIG. 2 shows a side view of an alternative sensor arrangement to that of FIG. 1.

A further example of a possible capacitive sensor arrangement which may be used is shown in FIG. 2. In any such embodiment, the occupancy detector 26 may comprise a charged electrode such that a change in the electric field due to the presence of an occupant in the seat 10 can be detected. In the example of FIG. 2, a transmitter electrode 26a and receiver electrode 26b are provided at spaced locations, thereby establishing an electric field 26c and current pathway there-between. The presence or absence of an occupant in the seat 10 is therefore determined according to a perturbation/change in the electric field. In this manner the impedance between the electrodes can be measured to determine the presence or absence of a passenger. Also, as in FIG. 1, the spacing and area of the electrodes can be tailored so that the effective detection range is sufficient to protrude slightly beyond the cover 16 of the seat base 18.

In this manner, by using planar electrodes of known material and area, it is possible to make assumptions about the approximate area and properties of a human body in order to identify a human occupant as opposed to baggage or the like.

It is possible that other non-contact capacitive occupancy sensor 26 arrangements may be considered. For any such variants, the spacing between the occupant in the seat 10 and a charged electrode/antenna may be assumed to be approximately constant and so threshold values of sensor readings can be defined to distinguish between a human occupant and other types of articles placed on the seat. In any such embodiments the length/area of the electrode/antenna can be predetermined to suit the given implementation and assumptions can be made about the properties and/or size of a human occupant as necessary to distinguish an occupant from other objects.

The occupancy sensor 26 can be retrofit to existing seating on a vehicle or can be integrated as part of a new-build seat. It has been found that an advantageous location for the sensor is on the underside of the seat base 18. This allows for the simple retrofit of the sensor 26 to the seat 10 and requires no modification or removal of foam or fabric. The underside of the seat 10 is rigid with foam/padding structure and fabric above. Locating the sensor on the frame means that the sensor is fixed and stable, thereby avoiding movement due to compression of the seat padding in use. One benefit of providing a non-contact sensor, rather than a conventional occupation sensor within the flexible portion of the seat membrane/cover 16 is that a fixed, non-contact sensor can offer improved operational life.

Also, the location of the sensor beneath the seat and the tailoring of the sensing range through antenna sizing means that the sensor is unlikely to generate false occupancy readings.

In this manner, it is also beneficial that the mounting of the non-contact sensor 26 to the rigid frame provides a fixed reference location for the occupation detector 26 for accurate determination of the occupancy status of a seat. This can improve the sensor performance and reliability. The sensor can be calibrated to account for measurements taken through the seat base padding/foam of upholstery 14 and cover 16.

It is an important practical feature—at least in part due to the sensitivity of non-contact capacitive sensors—that the occupancy sensors can also self-calibrate with respect to the seat material and the environment in use such that a common sensor module can be applied to different seat types. That is to say, once the sensor is installed, the sensor is able to determine the environmental operational parameter(s) in an unoccupied state and thereby adjust thresholds required for determination of an occupied state accordingly. Thus a relatively simple calibration routine is provided such that the sensor adjusts to its environment and updates the relevant threshold values upon start-up or else after successive instances or time periods of use.

With reference to FIG. 1, there is also shown an example of a second sensor 28, which takes the form of a radio communication device. The device 28 takes the form of a powered radio frequency field generating circuit and antenna arrangement. The device is preferably a Near Field Communication device and may adhere to conventional short-range wireless communication standards. In this regard, the range of operation (i.e. the permissible distance between the device 28 and a target device) is schematically indicated in FIG. 1 and may be less that 20 cm and typically less than 10 cm, such as, for example 4 or 5 cm.

The generation of a radio frequency field by the device allows a passive target device within range to be powered by device 28 for data transfer there-between. The target device (not shown) thus comprises a radio frequency antenna and a memory containing data to be interrogated by the device 28. Thus conventional RFID chips, tags, fobs or cards may be used as passive target devices. Also mobile communication devices, such as mobile telephones, i.e. smartphones, tablet computers, PDA's or the like may be configured for communication with the device 28.

The second sensor 28 is shown in FIG. 1 mounted in the arm rest 24 of the seat. The sensor 28 may be embedded in a molded material of an arm rest 24. This provides a particularly convenient location for access by a user and also allows a suitable icon or other usage indicia to be provided in prominent view on the surface of the arm rest 24. However, whilst such an embodiment may be advantageous for new seats or for retrofitting/refurbishing seats in which an entire arm module can be replaced, it is acknowledged that it may be more cost-effective to provide a communication module comprising the device 28 in another location. Such a module or "podded" sensor device may be mounted for example on a seat cover, a seat back (i.e. for access by the passenger behind the seat) or on a table or other fixture adjacent the seat. Any such arrangement may allow for flexible and/or cost-effective installation and cable routing as well as device maintenance.

The seat 10 of FIG. 1 also comprises a seat controller 30, which takes the form of a processor, such as a conventional programmable logic device or chip, having multiple inputs. The seat controller 30 may be an embedded microprocessor and may be formed as part of a module including one of the sensor 26 or 28 arrangements. The sensor 26 or 28 raises a General Purpose Input Output (GPIO) line on the seat controller 30 to indicate occupancy state.

Figure 3:
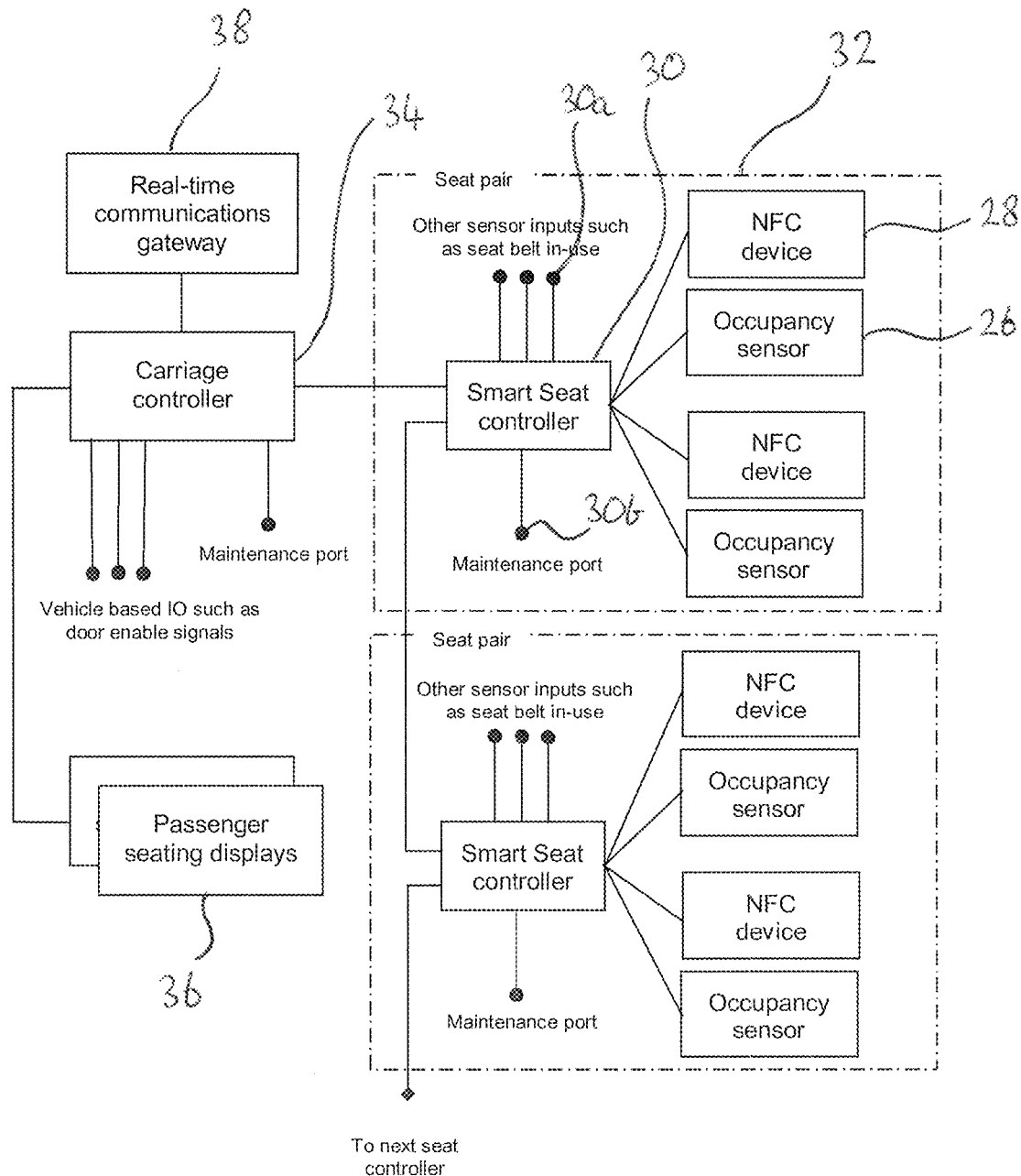
FIG. 3 shows a schematic circuit arrangement of a plurality of seats according to the invention.

The seat controller and electrical/communication system in which multiple seats 10 may be used is described in further detail with reference to FIGS. 3 and 4.

A seat controller 30 may be provided for each seat. However in the event that seats are arranged, for example within a cabin or carriage in rows of two or more seats, a single seat controller 30 may advantageously serve a plurality of seats, such as a seat pair 32 as shown in FIG. 3. The seat controller 30 receives the outputs of the sensors 26 and 28 and performs some local processing to determine the occupancy status of the seat(s) 10. The seat controller 30 may analyze sensor inputs and compare the readings to predetermined threshold criteria in order to provide a simplified occupancy signal output.

Each seat controller 30 includes additional input lines 30a to the sensor inputs described above. Such additional inputs allow the system to be configurable to accept further sensor inputs which may further be used to validate a determination of seat occupancy. For example, the further inputs may relate to vehicle-related input/outputs, a seatbelt usage sensor, a weight sensor in the seat, or other seat-related equipment usage sensors. In other embodiments of the invention, one or more of such alternative inputs may be used in place of the first sensor described above.

Additionally or alternatively, a further input line for the seat controller 30b may be redundant in normal use and may provide for a maintenance port so that updates can be provided to the seat controllers 30 as necessary after installation.

In certain examples of the invention, the seat 10 may also have a speaker and/or display screen 36 to convey information to an occupant.

For a passenger vehicle a central vehicle or cabin/carriage controller 34 is provided. Depending on the type of vehicle and its size/layout, a central controller 34 may be provided for the whole vehicle, or a part thereof. The central controller 34 is arranged to receive the output of the seat controllers 30 connected thereto.

A local network is established wherein each of the seat controllers 30 are connected to the central controller 34 such that each seat controller 30 can communicate therewith. A wired or wireless network on-board the vehicle may be established for this purpose. In the present embodiment, a wired network is established, wherein each seat controller 30 is connected in series to the central controller 34, so as to form a so-called 'daisy chain' of controllers in the network. This provides for simple wired connections. Wired network options are implemented by configuring the front-end communication interface of the seat 10 and vehicle controllers and may include: power-line communications; CAN bus; RS484; or Ethernet embodiments. Wireless network options may include for example: ZigBee/802.15.4; 802.11b/g/n; ISM 868 or 433.

The on-board network in this embodiment also includes a visual display screen 36 and/or speaker for each seat 10 or seat pair/row 32. The display screen 36 is used to provide a visual indication of the occupation status of each seat and/or to provide passenger instruction to validate a ticket or other identification means using the second sensor 28. Additionally or alternatively a speaker may be used to provide announcements to the occupier. In such embodiments the passenger seating display screens 36 or speakers are collectively controlled by the central controller 34 but could alternatively be individually controlled by the corresponding seat controller 30 if required. Additionally or alternatively one or more common display screen 36 or speakers may be provided for a plurality of seats or the entire vehicle/carriage.

The central controller 34 comprises, or is in communication with, a communications gateway 38 so as to allow transmission and receipt of data signals from outside of the vehicle. Thus the central controller 34 may have associated therewith a central data store for the carriage/vehicle and can receive data concerning ticket/code validity and/or reservations for each journey. The central controller 34 can thus be updated in advance of a journey and/or in real-time during a journey and can accordingly update seat controllers 30 as necessary. Such a communication gateway 38 may make use of one, or typically, a plurality of wireless communication standards, including those used in mobile telephony networks, such as GSM, 3G, EDGE or similar. Such communication means allow occupancy data to be transmitted substantially in real-time as part of a wider control/monitoring system. Additionally or alternatively, the central controller 34 may communicate with one or more further devices on-board the vehicle, typically via wireless communication, using for example Wi-Fi® or Bluetooth® standards.

The operation of one example of a system according to the invention will now be described with reference to FIGS. 4a and 4b below.

The seats in a vehicle cabin 40, such as a train carriage, are initially in an unoccupied state. On detecting that a seat is occupied by way of a corresponding signal from occupancy detector 26, the seat controller 30 enables the NFC device 28, providing the capability for validation of smart tickets (e.g. having an RFID tag/chip therein) and/or communication with the passenger through applications provided on a suitable portable communications device utilizing NFC.

If a connection is established by the passenger bringing the relevant ticket or device into proximity of the reader device 28, a code is received and fed to the seat controller 30. The NFC device 28 communicates to the seat controller 30 over a serial bus interface which provides set-up information to the embedded NFC device and return communications from the device. The received code can then be checked by the seat controller 30 against existing records to determine the validity of the code.

It will be appreciated that codes may comprise simple alphanumeric strings or more complex multi-part codes comprising any or any combination of: time/date data; journey data; carriage, vehicle or seating class data; and/or an individual seat identifier, for example in the case of reserved seating. Conventional seating row and seat numbering may be used in order to identify individual seats.

Visual indication of ticket/code validation is provided to the passenger, for example via the display screen 36 or some other indication means, such as a simple LED provided with the NFC device 28. A ticket shall be valid if the following conditions are met:

The ticket is valid for the journey (route operator, time of day etc.)

The passenger is in the appropriate class of seat based on the ticket purchased

The passenger is occupying the correct seat if seat reservations are in place

The NFC device 28 also enables communication with the passenger and can be used to:

Validate smart tickets that use RFID technology

Validate smart tickets using NFC to a smart device holding the ticket

Provide a communication channel between the vehicle operator and the passenger

The seat controller 30 stores and communicates a seat occupancy and validation status to the central controller 34 such that account of all seats 10 within the vehicle 40 is maintained thereby. The information maintained for each seat comprises:

Occupancy state

'Occupied from' location

Validity of ticket/code

Status of other vehicle based I/O or sensors, such as seatbelt in use

Passenger communications through NFC enabled apps or other audio/visual display means.

The seat controller 30 is location specific within a vehicle and contains a programmable address in non-volatile memory which identifies its location and the seat numbers monitored. The seat controller 30 maintenance interface 30b may be used to program the seat address, enable or disable seat controller 30 functionality and/or gather performance data.

Using the above described system, the central controller 34 can maintain a model of the vehicle and its corresponding occupancy status as shown in FIG. 4b. The central controller 34 can thus control the output of a visual display 36 indicating the occupancy state of each seat. The display 36 may be provided on a fixed screen, for example located in a driver/conductor cabin. In the present embodiment central controller 34 can output the relevant data to a portable device, such as a tablet computer or similar communications device 42 to be carried by a conductor 44 or other vehicle crew member. Thus the crew member can carry a device 42 displaying the occupancy status of each seat in real-time via a wireless interface with the central controller 34.

In one embodiment, the model of the vehicle comprises a seating plan 46 as shown in FIG. 4b, in which each seat has one of a predetermined number of states. Each different state may be indicated in the plan by color coding of the seat or else by providing some other visual/graphical indicia scheme. The different states of each seat in the model comprise:

Seats unoccupied

Seats unoccupied but reserved

Seats occupied requiring a ticket to be checked/validated

Seats occupied where ticket has been validated

Seats occupied where ticket is not valid (such as standard class ticket in first class)

Seats occupied where ticket is no longer valid

Thus it will be appreciated that a seat status may comprise three different status indicators comprising an occupation indicator, a reservation indicator and an occupant validation indicator. The interplay between these three status indicators is particularly important to vehicle operators and allows seat allocation to be managed in ways which have not been hitherto possible. For example, it allows tickets to be sold and/or seat reservations made or relinquished even whilst a train is undergoing a journey. Thus seat transactions can be undertaken during a vehicle journey right up to the point at which a train arrives at an embarkation location for a particular ticket. This ability to monitor and change seat allocations in real time (i.e. during a current instance of vehicle operation, rather than before a particular journey has commenced) can significantly increase the efficiency of usage of the available seating capacity on the vehicle.

Further textual auxiliary information shall also be available to the crew such as occupancy start/end location, reservation start/end location, or similar. Such auxiliary information may be accessed for example by selecting one of the seats in the seating plan on screen.

The carriage controller 34 may also communicate the state of each seat using displays located at the entrance to the vehicle or at key passenger flow points. Showing where seats are available at such locations may help to improve passenger flow and the passenger experience. A simplified color coding scheme may be used for such displays 36.

In addition to, or as an alternative to, the onboard seat occupancy monitoring system described above, the central controller 34 may maintain and communicate the state of each seat to a remote server 46, 48 using the remote communication gateway 38 utilizing cellular communications via existing cellular carrier network base stations 50. In one embodiment, the remote server 46 comprises a centralized control/monitoring center or service provider system. This data may be used for:

Passenger counting (including identifying number of passengers in each vehicle seating class)

Journey analysis tracking ticket use with respect to passengers, stations and services Passenger flow control informing passengers at forward stations of availability and location of seating on each service An open interface standard is provided for communication with third party systems such as station Customer Information Systems (CIS).

The central on-board vehicle controller 34 uses geo-location data from the real-time communication gateway 38 and/or GPS location information, possibly in conjunction with other vehicle based inputs/outputs such as door signals, vehicle speed or the like to build an intelligent state of seat occupancy and ticket validity.

In one development, the vehicle controller 34 or remote server 46 may communicate with a station server 48 for a station on the planned vehicle journey. Thus information on vehicle occupancy can be sent to the station in advance of the arrival of a train, to indicate occupancy status to passengers and staff at the station. Similarly, occupancy status can be sent to ticketing offices or other sales functions to give an account of seating availability substantially in real time.

In embodiments in which the central controller 34 is provided for individual carriages, a further vehicle controller 34 may or may not be provided. The carriage controllers may have a programmable address in non-volatile memory which identifies their respective location in the vehicle. As with the seat controllers 30, the central carriage controller 34 includes a maintenance interface to program the carriage address, enable functionality/devices and gather performance data.

In one embodiment, one of the seating controllers 30 may be customized to provide a central carriage or vehicle controller 34.

In some embodiments it is desirable that the central data store on board the vehicle is used to provide robust local storage of occupancy and/or other safety-related parameters. Such data may be particularly important in the event of an accident or other emergency. Particularly in embodiments in which a seat belt sensor or other safety sensor is provided, the central data store may provide a record of behavior or other factors which can be accessed in real time or after an event.

Additionally or alternatively, any of the data storage device described above may be used to provide one or more other record of events or passenger behavior. For example, the data store may provide a record of whether and/or when one or more passenger announcements or other passenger information has been provided by passenger information systems on board the vehicle. Such passenger information may be important in determining whether penalty fares for non-ticket-holding passengers can be applied. Also a log of safety announcements, for example regarding seatbelt use or passenger movement within the vehicle or other protocols or requirements may be maintained on the central or local seat data stores. Typically such announcements will be controlled and recorded on a vehicle/cabin level but individual seat implementation is also a possibility. For example, occupants may individually acknowledge that the relevant information has been received.

The present invention as described above provides a new-build or retro-fit solution that can be easily maintained. The provision of smart ticket reading at the seat allows passengers to self-validate tickets, thereby reducing the need for manual checks and improving revenue protection for the vehicle operator. When provided as part of a larger monitoring system, the invention can provide benefits in accurate passenger counting, revenue protection, passenger flow control and journey analysis. The system can also provide useful feedback on purchased ticket usage to the vehicle operators.

Also the seat controller is adaptable in its function dependent on requirements and sensors/devices connected and can thus provide varying levels of sophistication including, for example:

Occupancy sensing only

Occupancy sensing with seat belt use

Occupancy sensing with NFC capability

Occupancy sensing with seat belt use and NFC capability

The system of the present invention can be deployed in various transport sectors including rail, bus, tram and marine applications.

What is claimed is:

1. A seat for a passenger vehicle, the seat comprising:
    a first sensor for detecting the presence or absence of an occupant in the seat; and
    a second sensor for validating the seat occupancy based on a received validation code and a reservation record pertaining to the seat by:
        identifying occupant identity information from the received validation code;
        identifying the reservation record; and
        comparing the occupant identity information and the reservation record to determine whether the occupancy of the seat is valid,
    wherein the seat further comprises a transmitter for transmitting a signal indicative of valid occupancy of the seat and wherein, in use, the occupancy data is transmitted to and from the vehicle during transit of the vehicle for updating the reservation record substantially in real-time with at least one of the comparing or a current vehicle journey.

2. The seat according to claim 1, wherein the first sensor comprises a capacitive non-contact sensor.

3. The seat according to claim 2, wherein the first sensor comprises a charged electrode of predetermined area calibrated and mounted relative to the seat so as to define an operational range which extends only slightly beyond an occupant contacting portion of the seat.

4. The seat according to claim 2, wherein the first sensor has an operation range of between 5 and 50 cm.

5. The seat according to claim 1, wherein the first sensor is calibrated so as to have one or more threshold values indicative of a difference between a human occupant and other articles occupying the seat.

6. The seat according to claim 1, wherein the first sensor has a self calibration routine for determining one or more environmental condition and adjusting one or more threshold values indicative of seat occupant detection.

7. The seat according claim 1, wherein the seat comprises a rigid support and upholstery mounted thereon, wherein the first sensor is mounted to the rigid support.

8. The seat according to claim 1, wherein the second sensor comprises a wireless radio frequency communication device comprising a near field communication device.

9. The seat according to claim 1, wherein the second sensor is provided in an arm-rest portion of the seat or else maintained within a cover material of the seat.

10. The seat according to claim 1, further comprising:
a controller arranged to receive signals from the first and second sensors and to control transmission of the signal indicative of valid occupancy of the seat in dependence thereon, wherein the controller is arranged to receive a code via the second sensor and compare the code against one or more pre-stored codes in order to determine a valid occupation status of the seat.

11. The seat according to claim 10, wherein the seat comprises transceiver means and the controller receives updates of valid codes from a remote location external to the vehicle.

12. The seat according to claim 1, wherein, in use, the occupancy data is transmitted for updating the reservation record based on whether occupancy of the seat is valid.

13. A passenger vehicle occupancy monitoring system comprising a plurality of seats according to claim 1 and a central controller onboard the vehicle, wherein the central controller is arranged to receive occupation status signals for each seat via a local communication network by:
identifying occupant identity information from a validation code;
identifying a reservation record pertaining to a seat of the plurality of seats; and
comparing occupant the identity information and the reservation record to determine whether the occupancy of the seat is valid based on the validation code and the reservation record;
wherein the central controller is arranged to update the reservation record for each seat substantially in real-time with at least one of the comparing or the current vehicle journey.

14. An occupancy monitoring system according to claim 13, comprising seat controllers arranged to receive signals from the first and second sensors of each seat and to control transmission of the signal indicative of valid occupancy of each seat to the central controller.

15. The occupancy monitoring system according to claim 13, wherein the central controller controls output of a vehicle seating plan, said seating plan comprising at least one of an occupancy status or a reservation status for each seat.

16. The occupancy monitoring system according to claim 15, wherein the plan comprises a color coding scheme indicative of at least one of the occupancy status or the reservation status of each seat.

17. The occupancy monitoring system according to claim 13, wherein at least one of predetermined seat validation or reservation information is stored in advance for one or more journeys.

18. The occupancy monitoring system according to claim 13, wherein the system further comprises a portable communication device for use by a member of vehicle crew on board said vehicle, said device having a display screen and being in communication with the central controller.

19. The occupancy monitoring system according to claim 13, wherein the central controller is arranged to update the reservation record based on whether occupancy of the seat is valid.

20. The occupancy monitoring system according to claim 13, wherein the central controller is arranged to update the reservation record for each seat in substantially real-time with the current vehicle journey.

* * * * *